United States Patent [19]
Bland et al.

[11] Patent Number: 5,547,987
[45] Date of Patent: Aug. 20, 1996

[54] PATHOGEN INHIBITOR FOR ANIMAL FEEDS

[75] Inventors: Bobby J. Bland, Buford; Kurt E. Richardson, Hoschton, both of Ga.

[73] Assignee: Anitox Corporation, Buford, Ga.

[21] Appl. No.: 92,788

[22] Filed: Jul. 19, 1993

[51] Int. Cl.$^6$ .................................................. A01N 37/00
[52] U.S. Cl. .................................................. 514/557
[58] Field of Search ............................................. 514/557

[56] References Cited

U.S. PATENT DOCUMENTS 3,595,665  7/1971  Huitson et al. ...................... 514/557
3,895,116  7/1975  Herting et al. ...................... 514/557
4,183,953  1/1980  Skou et al. .......................... 424/317

OTHER PUBLICATIONS

Merck Index, 10th Ed. (1983) pp. 1562 and 7730.

*Primary Examiner*—Allen J. Robinson
*Attorney, Agent, or Firm*—Oblon, Spivak, McClelland, Maier, & Neustadt, P.C.

[57] ABSTRACT

A composition and method for inhibiting the growth of pathogens in animal feeds is disclosed. The active ingredient is a mixture of n-butyric acid and propionic acid, each partially or completed converted to one of its salt forms.

10 Claims, No Drawings

PATHOGEN INHIBITOR FOR ANIMAL FEEDS

BACKGROUND OF THE INVENTION

1. Field of the Invention

This invention provides a chemical preservative for cereal grains, rendered animal by-products, silage, and complete animal feeds to prevent deterioration by fungus and bacteria and the formation of mycotoxins by the combined use of a n-butyric acid salt and a propionic acid salt.

1. Discussion of the Background

It is common practice to use fungicides in animal feedstuffs. The typical fungicide contains propionic acid or its sodium, calcium or ammonium salt in some form. Some commercial products are granular materials consisting of liquid propionic acid dispersed on a carrier. Others include aqueous solutions of propionic acid and aqueous solutions of ammonium propionate. Attempts have been made to improve the antifungal activity of propionic acid and its salts by combining them with a second volatile fatty acid and in some cases an improvement was observed although usually the results were disappointing. For instance, in 1973 the U.S. Grain Marketing Research Center of the U.S. Department of Agriculture at Manhattan, Kansas, issued a report entitled "Grain Preservatives for High-Moisture Feed Grain" by Dr. David Sauer. It was found that propionic acid alone was far superior to mixtures of propionic:formic, propionic:acetic, and propionic:isobutyric in all ratios tested.

Huitson et al, U.S. Pat. No. 3,595,665 disclosed a method for preventing mold growth in crops and animal feedstuffs during storage based on binary and ternary mixtures of lower carboxylic acids. In this case, it appeared that acetic/propionic acid and formic/acetic/propionic acid mixtures were more effective than the individual acids. Mixtures containing propionic acid and n-butyric acid or isobutyric acid were not investigated.

Herting et al, Cereal Chem. 51:382–388 (1974) reported that isobutyric acid is the most effective antifungal agent among the common $C_1$–$C_4$ acids and that mixtures such as propionic:n-butyric:water (25:25:50) and propionic:isobutyric:water (25:25:50) are more effective than the individual acids in water. It was found that activity depended on the amount of water in the mixture; surprisingly, the activity increased as the proportion of water was increased. However, the presence or absence of mold was determined visually which is too imprecise method to draw valid conclusions.

Skov et al, U.S. Pat. No. 4,183,953 added isobutyric acid to aqueous ammonium isobutyrate in order to lower the crystallization temperature from 32° F. to about −20° to −40° F., thus enabling the use of ammonium isobutyrate solutions in unheated areas in cold weather. The relative antifungal activities of ammonium isobutyrate alone vs. isobutyric acid/ammonium isobutyrate were not reported. We have tested similar mixtures of propionic acid and ammonium propionate, at different ratios and pH values, and found no improvement in biological activity.

It is known that n-butyric acid, like isobutyric acid, is an effective fungicide. However, it smells even worse than isobutyric acid and has not been used commercially. Many salts of n-butyric acid are less malodorous than the free acid, but are still highly objectionable to users and to the livestock who must eat the treated feed. Therefore, neither n-butyric acid nor its salts have been considered to have any practical utility as an animal feed preservative. We have discovered that n-butyric acid and its salts exhibit a strongly synergistic microbial-inhibiting effect in combination with salts of propionic acid. Further, we observed that n-butyrate/propionate mixtures are significantly more effective than isobutyrate/propionate mixtures. Therefore, the effective quantity of n-butyrate mixtures can be reduced to the point where the presence of n-butyric acid and its salts is no longer objectionable. This effect provides true utility for n-butyric acid in the field of animal feedstuffs for the first time, and represents one of the few commercial applications available for this material considering its terrible smell.

SUMMARY OF THE INVENTION

An object of the invention is to provide a method for inhibiting the growth of pathogens in animal feedstuffs comprising: applying to a feedstuff an effective growth-inhibiting amount of a mixture containing n-butyric acid and propionic acid in a ratio of 3:1 to 1:3 wherein 75–100 mol % of the acid mixture is in the form of an alkali, alkaline earth or ammonium salt.

Another object of the invention is to provide a composition useful for inhibiting the growth of pathogens in animal feedstuffs comprising n-butyric acid and propionic acid in a ratio of 3:1 to 1:3 wherein 75–100 mol % of the acid mixture is in the form of an alkali, alkaline earth or ammonium salt.

DETAILED DESCRIPTION OF THE PREFERRED EMBODIMENTS

The preservative composition of this invention contains a mixture of n-butyric acid and propionic acid, each partially or completely converted to one of its salt forms. The ammonium salts are conveniently obtained by adding anhydrous ammonia to an aqueous solution of the acids to form a buffered mixture at pH 7±1, preferably 7±0.2. Neutral pH is favored in order to reduce the corrosive properties and odors of the carboxylic acids.

When applied to feedstuffs in aqueous solution, the present invention contains 10–50 wt. % water and 90–50 wt. % of an n-butyrate/propionate mixture in a ratio of 3:1 to 1:3 wherein 75–100 mol. % of the acid mixture is in the form of a salt. Preferably, 80–90 mol. % of the acid mixture is in salt form, providing a buffered solution. Preferred ratios of the $C_4/C_3$ species in the mixture are 60:40 to 40:60, typically 50:50. The total quantity of each carboxylic acid in the mixture, calculated on a free acid basis, is between 35 and 15 wt. %, preferably 25–33 wt. %.

Propionic acid is supplied in commercial quantities by Eastman Chemical Co., Hoechst Celanese, and Union Carbide. It is produced from petroleum products such as liquid phase oxidation of butane or carboxylation of ethylene. n-Butyric acid is supplied in commercial quantities by Hoechst Celanese. It is produced by liquid phase oxidation of butane.

Other suitable salts of these acids include the alkali metal salts, such as sodium and potassium, and the alkaline earth metals, e.g., magnesium and calcium. Alkali metal and alkaline earth metal salts are easily prepared by treating the mixture of n-butyric acid and propionic acid with the desired metal hydroxide or carbonate in aqueous solution. The two carboxylate salts can be prepared separately and combined, optionally with additional n-butyric acid and/or propionic acid if a buffered mixture is desired. Ammonium salts can be prepared by treating the free acid with water and ammonium hydroxide or anhydrous ammonia. Anhydrous ammonia is supplied in commercial quantities by LaRoche Industries, and National Ammonia Co. It is produced by reaction of nitrogen from the air with hydrogen obtained from natural gas using a catalyst and pressure to produce anhydrous ammonia.

In actual commercial use of feed fungicides, the product is generally added to the animal feedstuff at some point where it can be conveniently mixed thoroughly into the feedstuff. The preferred means of addition is by a general purpose feed mixer where all ingredients in the feed are mixed together at one time. Another possible point of addition is in a screw conveyor by means of a spray nozzle while the feed is being carried along by the conveyor.

The present fungicide can be added as a liquid spray containing the n-butyrate/propionate mixture in water, or as a granular powder composed of 20–60% dry weight of the active ingredient mixture dispersed on inorganic substances such as vermiculite, verxite, silicon oxides, and absorbent clays. Organic materials such as ground corn cobs are also suitable carriers.

The present invention can be used to control the growth of the predominant types of microorganisms found in foodstuffs including Aspergillus, Fusarium, Penicillium, Rhizopus, Mucor and yeast. Representative foodstuffs include broiler starter, broiler grower, broiler finisher, layer feeds, breeder feeds, swine feeds of all types, cattle feeds of all types, horse feeds, pet foods, and specialty feeds such as shrimp, catfish, and eel feeds. These feeds are all specially formulated to give best results in the species of animal or fish being fed. They contain varying amounts of cereal grains, vegetable protein meals, animal protein meals, vitamins, minerals and special additives such as fungicides, antibiotics, drugs, etc. Sometimes fungicides are added to the cereal grains to protect the grains during storage prior to use.

Cereal grains—Examples include but are not limited to the following: corn, sorghum (milo), wheat, oat, rye, and barley. The preferred application rate for cereal grains is 0.05%–1.0 wt. % for liquid solutions and 0.1% to 2.0 wt. % for powder treatment.

Rendered animal by-products—Examples include but are not limited to the following: meat and bone meal, feather meal, poultry viscera meal, fish meal, and blood meal. The preferred application rate for rendered animal products is 0.1–1.0 wt. % for liquid solutions and 0.1–2.0 wt. % for powder treatment.

Vegetable protein meals—Examples include but are not limited to the following: soybean meal, rapeseed meal, cottonseed meal and sunflower seed meal. The preferred application rate for vegetable protein meals is 0.05%–1.0 wt. % for liquid solutions and 0.1% to 2.0 wt. % for powder treatment.

Silage—Examples include but are not limited to the following: corn silage, wheat silage, sorghum silage, hay silage, and other grass silages. Preferred application rates vary from 0.05–1.0 wt. % for liquid solutions and 0.1–1.0 wt. % for powder treatment.

Finished feeds—Examples include but are not limited to the following: poultry starter feed, poultry grower feed, poultry layer feed, and poultry breeder feed. The preferred application rates for finished feed is 0.05–1.0 wt. % for liquid solutions and 0.1–1.0 wt. % for powder treatment.

Similar grades of swine feed, beef cattle feed, dairy cattle feed, horse feed, aquaculture feed, and pet feed are generally treated with 0.05–1.0 wt. % of liquid solutions and 0.1–1.0 wt. % of powder fungicide.

EXAMPLE 1

A bulk tanker trailer containing 20,000 kg of a 1:1 propionic acid:n-butyric acid mixture is delivered for unloading at the manufacturing site. The unloading valve on the bottom of the bulk tanker is connected to the unloading port of the station by a three inch chemical resistant hose. The valves at the reactor vessel and unloading port are opened prior to opening the unloading valve on the bulk tanker. The propionic acid:n-butyric acid mixture is pumped into the reactor vessel through three inch stainless steel pipe. After the contents of the tanker have been transferred to the reactor vessel, all valves are closed and the hose connecting the bulk tanker to the unloading station disconnected.

A metered volume of water (9,333 kg) is then added to the reactor vessel through a two inch polypropylene pipe. The water pipe enters the stainless steel reactor vessel through a two inch opening in the top of the reactor. The aqueous mixture is circulated within the reactor vessel by externally pumping the liquid from the bottom of the vessel to the top of the vessel through three inch stainless steel pipe. Anhydrous ammonia is gradually bubbled into the circulating aqueous propionic:butyric acid mixture by a stainless steel sparge. Ammonia is added to the mixture until the solution reaches a pH of 7±0.1. The ammonia content is 12.7 wt. %. The propionic acid:n-butyric acid mixture continues to circulate until the temperature of the solution falls below 100° F. The mixture is then transferred to a storage vessel.

EXAMPLE 2

Production of meat and bone meal in a continuous flow system: The raw meat and bone waste products are passed into a cooker and subsequently through a series of grinders. As the meat and bone meal passes along a 16 diameter inch screw conveyor at the rate of 5 tons per hour, a propionate:n-butyrate salt solution is sprayed as a mist onto the meat and bone meal. The composition of the solution is 30% propionic acid, 30% n-butyric acid, 12.7% ammonia and 27.3% water, all percentages by weight. A filter is placed prior to the pump to take out any particulates in the solution which would clog the nozzles. The liquid is supplied to stainless steel nozzles under pressure. The liquid and compressed air are mixed externally to produce a completely atomized spray through the nozzle. The spray nozzles are mounted in the top cover of the screw conveyor. There are two nozzles mounted 3 feet apart which deliver droplets in the range of 30–50 microns. The meat and bone meal is treated with 8 pounds of solution per ton. The pump is set to deliver 40 pounds per hour (8 lbs/ton×5 tons/hr=40 lbs/hr). After spraying, the meat and bone meal is conveyed into storage hoppers to await shipment.

EXAMPLE 3

A train carload containing 100 tons of whole kernel corn is unloaded into storage. As the corn drops out of the bottom of the car into a pit it is picked up by conveyors to move it to a bucket elevator. The conveyor leading to the bucket elevator is a 16 diameter inch screw conveyor. Four air atomizing nozzles, each with a capacity of 5 gallons per hour and delivering a droplet size of 40–80 microns, are mounted in the top cover of the screw conveyor at 3 foot intervals. The composition of the solution is 30% propionic acid, 30% butyric acid, 12.7% ammonia and 27.3% water, all percentages by weight. The corn is treated with three pounds of solution per ton while moving through the conveyor at a rate of 50 tons per hour. The application rate of the solution is 3 lbs/ton×50 tons/hr.=150 lbs/hr. After treatment, the corn moves into the bucket elevator which carries it up and drops it into the storage bin.

EXAMPLE 4

Ensiling of whole plant corn: The whole plant corn is harvested and chopped in the field by a silage harvester. The chopped product is transported from the harvester to the silo by wagon. As the chopped silage is unloaded from the wagon by a 6 inch diameter screw conveyor at the rate of 6 tons/hour, a propionic acid:butyric acid salt solution is sprayed as a mist onto the chopped corn silage. Composition of the solution is 30% propionic acid, 30% butyric acid, 12.7% ammonia and 27.3% water, all percentages by weight. A filter is placed prior to the pump to take out any particulates in the solution which would clog the nozzles. The liquid is supplied to stainless steel nozzles under pressure. The liquid and compressed air are mixed externally to produce a completely atomized spray through the nozzle. The spray nozzles are mounted in the top cover of the screw conveyor. There are two nozzles mounted 3 feet apart which deliver droplets in the range of 30–50 microns. The chopped silage is treated with 40 pounds of solution per ton. The pump is set to deliver 240 pounds of solution per hour (40 lbs/ton×6 tons/hr=240 lbs/hr). After spraying the chopped silage is conveyed into the silo for fermentation.

EXAMPLE 5

A three ton batch of broiler grower pellets as a complete feed is made as follows. The batch is made in a feed mill using a three ton horizontal computer controlled mixer. The mixer design is such that the outside hull of the mixer is stationary and the mixing is done by rotating paddles inside the mixer. The ingredients for the batch are individually weighed into the weigh hopper which is directly above the mixer. The batch ingredients weighed into the weigh hopper are shown in Table 1:

TABLE 1

BROILER GROWER DIET

| Ingredient | Pounds |
| --- | --- |
| CORN | 2232 |
| MILO | 1560 |
| SOYBEAN MEAL | 1470 |
| FEATHER MEAL | 120 |
| POULTRY MEAL | 150 |
| FAT | 291 |
| VITAMIN | 6 |
| CHOLINE CHLORIDE - 70 | 3 |
| TRACE MINERALS | 6 |
| COPPER SULFATE | 3 |
| DEFLOURINATED PHOSPHATE | 84 |
| LIMESTONE | 31.8 |
| SALT | 13.2 |
| LYSINE | 3 |
| DL-METHIONINE | 12 |
| COCCIDIOSTAT | 6 |
| ANTIBIOTIC | 3 |

Once the ingredients are weighed and the mixer is clear of the previous batch, the contents of the weigh hopper are dropped directly into the mixer. This transfer takes only a few seconds. The paddles begin to turn, mixing the ingredients. The mixer hull is equipped with three air atomizing nozzles giving droplet sizes in the range of 40 to 80 microns. The fungicidal solution of Example 1 is sprayed while mixing the ingredients over a period of 40 seconds. The feed is mixed for an additional 4 minutes. After the additional mixing, the feed is dropped from the mixer into a holding tank below, the transfer taking a few seconds. The feed is then moved by a screw conveyor to an overhead surge bin. From this surge bin, it is transferred by gravity to a steam conditioning chamber to add moisture to the feed. From there the feed goes to a pelletizer which compresses the mash feed into small firm pellets under pressure and 175° F. temperature. After the pelletizer, the feed passes through a cooler to lower the temperature of the pellets to near ambient temperature and then to storage for shipment.

EXAMPLE 6

The anti-fungal activities of several propionate:n-butyrate mixtures were evaluated on corn by a method involving the measurement of respiratory carbon dioxide in the headspace gas of model feed storage tanks. The percent carbon dioxide in the headspace gas was determined by injecting a subsample into a gas chromatograph. This procedure is based on the long accepted fact that fungal activity is coupled to aerobic respiration and that the fungal degradation of carbohydrates results in the production of carbon dioxide, water, heat and fungal biomass according to the following equation:

$$C_{6n}H_{12n}O_{6n} + nO_2 \rightarrow nCO_2 + nH_2O + \text{fungal biomass} + \text{heat}$$

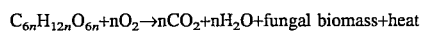

The advantages of measuring respiratory carbon dioxide are that carbon dioxide is a primary product of fungal activity, it is easily and accurately measured and it is applicable to unaltered feed under controlled moisture, temperature, and atmospheric conditions. In addition, it has been observed that there is a direct correlation between increasing carbon dioxide levels with a rise in feed temperature and increased fungal populations.

Procedure:

1. Locally purchased corn is finely ground through a Romer Mill, sieved through a no. 18 U.S. Standard screen and thoroughly remixed. Corn ground through a hammer mill can be used as a substitute.
2. Three ten gram subsamples are removed and placed in a forced draft oven set at 110° C. overnight for initial moisture determination.
3. After calculating the initial moisture level, 1000 g of the ground corn is placed in 1 gallon jars and the moisture level is adjusted to 17% by the addition of tap water. The jars are shaken to distribute the water and the moisture level is allowed to equilibrate overnight.
4. The 17% moisture cornmeal is sifted through a #18 U.S. Standard mesh screen to obtain a uniform particle size and break up any clumped feed, and all the cornmeal is remixed using a sample splitter, before removing 1000 g samples for treatment with the mold inhibitor solution.
5. One gram of liquid mold inhibitor is diluted with 2.5 ml of tap water to aid in distribution and applied to each 1000 g sample of cornmeal using a mixer equipped with a pressure assisted atomizing spray nozzle. After the treatment has been applied to the cornmeal, the system is rinsed with 2.5 ml of water and the cornmeal allowed to tumble for an additional 5 minutes. Control treatments receive 5.0 ml of tap water to compensate for the dilution treatments and rinsing of the application system during treatment. After mixing, the cornmeal is removed from the mixer, remixed using a sample splitter and 90 g subsamples (6 replicates/treatment) are distributed into 8 oz glass jars and capped with lids having butyl septa. The treatment jars are incubated at 27° C. for 1 week.

6. On a daily basis, the air in the headspace is analyzed for carbon dioxide concentration as an indicator of fungal growth. The headspace in each treatment jar is sampled by inserting a syringe through the butyl septum and removing 0.2 ml of air. The air sample is analyzed for percent carbon dioxide on a gas chromatograph with a thermal conductivity detector using the following parameters.

Column: Porapak Q 80/100 mesh size
Injector/Detection temperature: 40° C.
Column temperature: 40° C.
Carrier gas: Helium at 120 ml/min 7. Three 10 g subsamples of the remaining control treatment are removed for confirming the adjusted moisture level and three 10 g subsamples of the remaining control treatment are removed for determining the initial mold count of the feed. Mold identification is also performed to help determine the resistance or susceptibility of different lots of corn to treatments. The following table reports the measured percentage of $CO_2$ in the headspace and the percentage of growth inhibition averaged over six replicates on day 7.

TABLE 1

| TREATMENT | VALUE | PERCENT INHIBITION DAY 7 | PERCENT OF $CO_2$ |
|---|---|---|---|
| Control | Observed | 0 | 15.26 |
| 60 wt. % propionic acid, 13.78 wt. % ammonia - 1 kg/ton | Observed | 86.4 | 2.07 |
| 60 wt. % butyric acid, 11.60 wt. % ammonium - 1 kg/ton | Observed | 87.9 | 1.85 |
| 45 wt. % propionic acid, 15.0 wt. % butyric acid, 13.24 wt. % ammonia - 1 kg/ton | Predicted Observed | 86.8 92.5 | 2.02 1.14 |
| 30 wt. % propionic acid, 30 wt. % butyric acid, 12.69 wt. % ammonia - 1 kg/ton | Predicted Observed | 87.2 94.8 | 1.96 0.80 |
| 45 wt. % propionic acid, 45% wt. % butyric acid, 12.15 wt. % ammonia - 1 kg/ton | Predicted Observed | 87.5 93.4 | 1.91 1.00 |

EXAMPLE 7

The effectiveness of propionic acid salts in combination with n-butyric acid or isobutyric acid salts were compared. The moisture level of ground corn was determined to be 15% and was adjusted to be approximately 17% by the addition of water to the ground corn in 1 gallon jars. The moisture level was allowed to equilibrate for 24 hours at room temperature. Treatments were applied to the ground corn in a horizontal mixer equipped with an atomizing spray nozzle. The treated ground corn was passed through a sampler splitter and 90 g were distributed into sterile 8 oz. glass jar. Six replicates per treatment were incubated at 24° C., shaken daily, and sampled for respiratory $CO_2$ for a seven day period. The headspace in each jar was sampled for $CO_2$ by inserting a syringe through the butyl septum and removing 0.2 ml of headspace gas. The gas was analyzed for percent carbon dioxide on a gas chromatograph equipped with a thermal conductivity detector. Gas chromatograph parameters were as follows:

Column: Porapak Q, 80/100 Mesh size
Injector/Detector Temp: 40° C.
Column Temp: 40° C.
Carrier Gas: Helium

TABLE 2

| TREATMENT | VALUE | PERCENT INHIBITION DAY 7 | PERCENT OF $CO_2$ |
|---|---|---|---|
| Control | Observed | 0 | 19.25 |
| 60 wt. % propionic acid 13.8 wt. % ammonia | Observed | 47.5 | 10.10 |
| 60 wt. % isobutyric acid 11.6 wt. % ammonia | Observed | 10.5 | 17.22 |
| 30 wt. % butyric acid 11.6 wt. % ammonia | Observed | 25.0 | 14.44 |
| 30 wt. % propionic acid 30 wt. % n-butyric acid 12.7 wt. % ammonia | Observed Predicted | 67.0 36.3 | 6.36 12.27 |
| 30 wt. % propionic acid 30 wt. % isobutyric acid 12.7 wt. % ammonia | Observed Predicted | 0 29.0 | 25.92 13.66 |

Conclusion:

Table 1 shows that the ammonium salts of propionic acid and n-butyric acid are roughly equivalent in activity under these conditions. However, a strong synergistic effect can be seen in each mixture of propionate/n-butyrate tested. These values are statistically significant at a probability of 99% by chi square tests.

Table 2 shows that this effect is not observed in isobutyrate/propionate mixtures. In fact, there appears to be a strong negative synergism.

Numerous modifications of the present invention are possible in light of these teachings. It is, therefore, to be understood that within the scope of the appended claims, the invention may be practiced otherwise than as specifically described herein.

We claim:

1. A method for inhibiting the growth of mold in animal feedstuffs comprising: applying to a feedstuff an effective growth inhibiting amount of a mixture containing n-butyric acid and propionic acid in a ratio of 3:1 to 1:3 wherein 75:100 mol. % of the acid mixture is in the form of an ammonium salt.

2. The method according to claim 1 in which the feedstuff is selected from the group consisting of cereal grains, vegetable protein meals rendered animal by-products, silage and finished feeds.

3. The method of claim 1 wherein the applied mixture is an aqueous solution containing 15–35 wt. % of n-butyric acid and 15–35 wt. % propionic acid calculated on a free acid basis, wherein 80–90 mol. % of said acid mixture is in the form of a salt with ammonia.

4. The method of claim 1 wherein the ratio of n-butyric acid to propionic acid is from 60:40 to 40:60, calculated on a free acid basis.

5. The method of claim 1 wherein the applied mixture is a powder comprising 20–60% by weight of said growth inhibiting mixture dispersed on a carrier.

6. The method of claim 5 wherein the carrier is selected from the group consisting of vermiculite, verxite, silicon oxides, absorbent clays and ground corn cobs.

7. A composition useful for inhibiting the growth of mold in animal feedstuffs comprising n-butyric acid and propionic acid in a ratio of 3:1 to 1:3 wherein 75:100 mol. % of the acid mixture is in the form of an ammonium salt.

8. The composition of claim 7 comprising 15–35 wt. % of n-butyric acid and 15–35 wt. % of propionic acid, calculated on a free acid basis, wherein said salt is ammonium.

9. The composition of claim 7 comprising 25–33 wt. % n-butyric acid, 25–33 wt. % propionic acid, ammonia and water wherein the mixture has a pH of 6.0–8.0.

10. The composition of claim 7 comprising a carrier and 20–60 wt. % of a mixture containing n-butyric acid and propionic acid in a ratio of 3:1 to 1:3 wherein 89:90 mol. % of the acid mixture is in the form of an ammonium salt.

* * * * *